United States Patent [19]

Jarreau et al.

[11] 4,093,619

[45] June 6, 1978

[54] METHOD FOR OXIDIZING CINCHONA ALKALOIDS

[75] Inventors: Francois Xavier Jarreau; Jean-Jacques Koenig, both of Paris, France

[73] Assignee: Etablissements Nativelle S.A., Paris, France

[21] Appl. No.: 743,257

[22] Filed: Nov. 19, 1976

[30] Foreign Application Priority Data

Nov. 19, 1975  France ................................ 75 35383

[51] Int. Cl.$^2$ ...................... C07D 401/06; C07G 5/00
[52] U.S. Cl. .................................................. 260/284
[58] Field of Search ............................. 260/586 P, 284

[56] References Cited

U.S. PATENT DOCUMENTS

| | | | |
|---|---|---|---|
| 2,560,361 | 7/1951 | Morrell et al. | 260/586 P |
| 2,779,801 | 1/1957 | Finch et al. | 260/586 P |
| 3,655,743 | 4/1972 | Nickl et al. | 260/284 |

OTHER PUBLICATIONS

Homer Adkins et al., J. Am. Chem. Society, vol. 63, pp. 2381–2383, (1941).

*Primary Examiner*—Jose Tovar
*Attorney, Agent, or Firm*—Sughrue, Rothwell, Mion, Zinn and Macpeak

[57] ABSTRACT

Method of oxidizing cinchona alkaloids by reacting specific ketone with cinchona alkaloid in the presence of a strong base and aprotic solvent; following oxidation the oxo compound is reduced to the corresponding stereoisomer.

13 Claims, No Drawings

METHOD FOR OXIDIZING CINCHONA ALKALOIDS

The invention relates to a novel method of oxidizing cinchona alkaloids so as to convert them chemically into the corresponding stereoisomers.

There are various known methods of chemically converting major cinchona alkaloids into their stereoisomers by way of the corresponding 9-oxo compounds. In the known methods, the alcohol group in the 9-position is oxidized, followed by specific reduction of the carbonyl.

Oxidation is usually brought about by the Oppenauer method adapted by Woodward et al. (J.A.C.S. 1945, 67, 1425). This is followed by stereospecific reduction with diisobutyl aluminium hydride to obtain the erythro derivatives, quinine and quinidine, or with sodium borohydride to obtain the threo derivatives as described by Gutzwiller and Uskokovic, Helv. Chim. Acta, 1973, 56, 1494. More particularly, quinine can be converted into quinidine by oxidation of quinine followed by reduction of the intermediate quinidinone by the Meerwein-Pondorff-Verley method; the oxidation and reduction steps can be consecutively carried out without isolating the intermediate quinidinone. Methods of this kind are described e.g. in German Pat. Nos. 877,611 and 1,165,604.

In general, the cinchona alkaloid is first oxidized in an appropriate solvent in the presence of a hydride acceptor and an alkali-metal alcoolate, followed by reduction by adding isopropanol in the presence of an alkali-metal alcoolate.

These methods have the disadvantage of requiring reflux heating of the reaction mixture during the entire oxidation reaction.

The invention relates to a novel method of oxidizing cinchona alkaloids such as quinine, cinchonine or their dihydro derivatives, the method being workable at ambient temperature with a practically quantitative yield, so that the alkaloids can be converted into the respective stereoisomers easily and under good conditions.

In the method according to the invention, a cinchona alkaloid is oxidized by a ketone in the presence of a strong base such as an alkali-metal hydride in an aprotic solvent, after which the compound formed is reduced.

The method according to the invention applies more particularly to the major cinchona alkaloids having the general formula I:

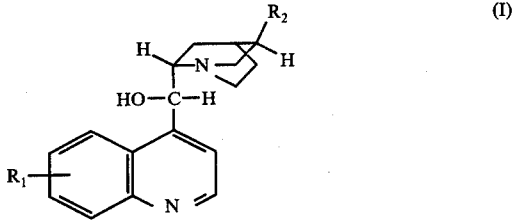

in which $R_1$ denotes a hydrogen atom, a lower alkyl group, a hydroxy group or an alkoxy group, and $R_2$ denotes a lower alkyl group or a lower alkenyl group.

In formula I hereinbefore, $R_1$ preferably denotes a methoxy group or a hydrogen atom in the 6' position in the quinolein ring. $R_2$ may be inter alia a vinyl group or an ethyl group.

In the method according to the invention, the formula I compounds are oxidized to the corresponding 9-oxo compounds having the general formula II:

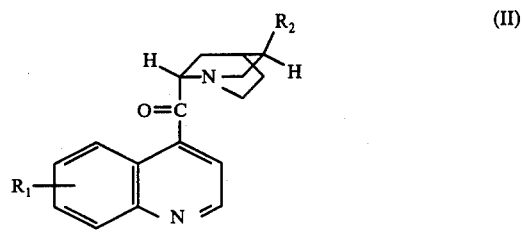

in which $R_1$ and $R_2$ have the same meaning as in formula I, under the action of a ketone in the presence of a strong base in an aprotic solvent.

The oxo-9 compounds having the formula II can subsequently be reduced by known methods to form a mixture containing the formula I compounds and their respective stereoisomers, which can be separated and isolated in conventional manner.

The ketone used in the method according to the invention for converting the formula (I) compounds can be represented by formula III:

$$R_3 - CO - R_4 \quad (III)$$

in which $R_3$ and $R_4$ are the same or different and represent an alkyl group, preferably a branched group such as t-butyl, or a phenyl or an aryl group, substituted if required; $R_3$ and $R_4$ may also together form a saturated or unsaturated ring having 5 or 7 carbon atoms or hetero-atoms, or a condensed ring.

The ketone used in the method according to the invention may be e.g. t-butyl ketone, cyclohexanone, benzophenone, fluorenone or a quinone, etc.

Although the cinchona alkaloid and ketone may react in equimolecular quantities, it is preferable to use an excess of ketone so as to improve the speed and output of the reaction.

The strong base can be an alkali-metal hydride, preferably sodium hydride or potassium hydride. Alternatively, other bases can be used such as an alkali-metal amide, preferably in excess.

Advantageously the oxidation reaction is carried out in an aprotic solvent such as an aromatic hydrocarbon e.g. toluene or benzene, a cyclic or open-chain ether e.g. tetrahydrofuran, dioxane, diglyme or diethyl ether, or an aprotic polar solvent such as dimethyl sulphoxide, dimethyl formamide or hexamethyl phosphotriamide, etc., or mixtures of these various solvents. It is not necessary to heat the reaction medium since the reaction is exothermic and can occur at ambient temperature. It may, however, be advantageous to heat slightly to a temperature not exceeding 100° C, depending on the nature of the solvent used, so as to accelerate the reaction.

The reaction can occur in air, but it is preferable to operate in an inert atmosphere, e.g. in a stream of nitrogen.

The method of oxidation according to the invention is applicable to the major alkaloids of cinchona, more particularly to cinchonine, quinine and their dihydro derivatives, which are oxidized to cinchonidinone, quinidinone or dihydro derivatives respectively. The alkaloids can be obtained by extraction from natural cinchona bark by the processes conventionally used in the art.

The method according to the invention is particularly advantageous for stereochemical conversion of the major cinchona alkaloids, since it can be used to obtain 9-oxo compounds with an excellent yield; the compounds can subsequently be reduced to form stereoisomers of the starting compounds. It is particularly advantageous to bring about stereochemical conversion directly without isolating the intermediate 9-oxo compound; the conversion is brought about under excellent conditions with a good yield, when the cinchona alkaloid is treated with an excess of ketone.

In a preferred embodiment of the method of oxidation according to the invention, the quinine base or cinchonine base is dissolved in an aprotic solvent such as tetrahydrofuran or dimethyl formamide in the presence of a slight excess of benzophenone or fluorenone. An inert gas is bubbled through the solution with agitation, after which potassium hydride or sodium hydride is progressively added.

When the reaction is practically complete, the product can be extracted with benzene, after hydrolysis. After evaporation of the solvent, purification and crystallization from diethyl ether, a practically quantitative yield of quinidinone or cinchonidinone is obtained. The thus-prepared quinidinone and cinchonidinone and, in general, the oxo compounds corresponding to the alkaloids chosen as the raw material, are important products inter alia as intermediates in the synthesis of compounds such as quinidine or cinchonidine which, owing to their pharmacological properties, can be used directly or in salt form in the treatment of various diseases, such as heart diseases, disturbances in rhythm and malaria.

For example, quinidinone can be reduced to quinidine, or cinchonidinone to cinchonidine, by the action of isopropanol in the presence of an alkali-metal alcoolate such as sodium isopropylate, with reflux heating in a solvent such as benzene or toluene.

The following examples illustrate the invention without limiting its scope.

EXAMPLE 1

6.4 g of quinine base and 5.4 g fluorenone were dissolved in 30 ml dimethyl formamide in a 100-ml 3-necked flask provided with a condenser, a nitrogen supply tube and a thermometer.

The solution was permanently agitated by a magnetic agitator; nitrogen was bubbled through for 15 minutes. Since the reaction was exothermic, 1.45 g sodium hydride was progressively added. The development of the reaction was followed in conventional manner, e.g. by thin-layer chromatography.

When the oxidation reaction was practically complete, the mixture was hydrolysed with 50 ml distilled water, followed by extraction with benzene. The organic phases were washed in water, then extracted with dilute hydrochloric acid.

The aqueous phases were collected and made alkaline with dilute caustic soda solution, then extracted with chloroform. After drying the chloroform phases on sodium sulphate, followed by filtration, the chloroform was evaporated to dryness.

The yield was 6.4 g of crude quinidinone in the form of a chestnut-brown oily liquid. The yield of crude product was quantitative.

Quinidinone can easily be identified after purification, by crystallization from diethyl ether.

Melting-point (Köfler bed): m.p. = 106°–107° C.

TLC silica gel plate G, chloroform/methanol solvent (90/10) Rf = 0.46 (Rf for quinine = 0.17). IR spectrum; $\nu$ C=O: 1685 cm$^{-1}$. Other characteristic absorptions: 1640, 1580, 1560, 1500, 1245, 1220 cm$^{-1}$.

NMR spectrum = 1.3 to 3.3 (1 OH, three wide superposed blocks). 3.9 (3H, s), 4.15 (1H, t), 4.8 to 5.2 (2H), 5.6 to 6.2 (1H, m), 7.2 to 8.9 (5H, m) ppm (CDCl$_3$ 60 MHz).

EXAMPLE 2

The method was the same as in Example 1; 6.4 g quinine and 5.8 g fluorenone were dissolved in 30 ml pure tetrahydrofuran.

The oxidation reaction was brought about in the same manner as before by agitation in a nitrogen atmosphere, by progressively adding 2 g potassium hydride.

After hydrolysis, extraction and purification by crystallization by the method described in Example 1, the yield was 5.6 g of pale yellow quinidinone crystals identified by chromatography (78% yield of the pure product).

EXAMPLE 3

The method was the same as in Example 1; 6 g quinine base and 5.4 g fluorenone were dissolved in 30 ml distilled dioxane.

After bubbling nitrogen for 15 minutes, 2.3 g sodium amide was progressively added, with continuous agitation. The reaction was accelerated by slight heating on a water bath at 60° C.

When the oxidation reaction was complete, the mixture was hydrolysed and extracted as indicated in Example 1.

The product was crystallized from diethyl ether, yielding 5.5 g quinidinone crystals identified by chromatography, the yield being 81% of pure product.

EXAMPLE 4

The method was the same as before, 6 g quinine and 6.3 benzophenone being dissolved in 30 ml tetrahydrofurane.

The reaction was brought about as in Example 1 in a nitrogen atmosphere, by progressively adding 1.5 g sodium hydride, thus obtaining 5.8 g crystals of quinidinone crystallised from diethyl ether (80% yield of the pure product).

EXAMPLE 5

The method was the same as in Example 1, 6.4 g quinine and 6.1 g fluorenone being dissolved in 30 ml dioxane and 2 g sodium hydride being added.

After about 3 hours, without isolating the quinidinone formed, a reduction reaction was brought about by adding 20 ml of isopropanol followed by heating so as progressively to eliminate the acetone formed.

At the end of the reduction, the mixture was hydrolysed with dilute hydrochloric acid and the aqueous phase was washed with benzene. The aqueous phase was made alkaline, followed by extraction with chloroform, drying of the chloroform phases on sodium sulphate, filtration and evaporation of the solvent to dryness.

6.1 g of a mixture consisting mainly of quinidine and quinine was obtained. 2.6 g of quinidine crystals were obtained by recrystallization from ethanol and had a melting point of 172°–3° C.

$\alpha_D^{25} = +264$ (ethanol, c = 1).

EXAMPLE 6

The method was the same as in Example 1, 6 g dihydroquinine and 5.9 g fluorenone being dissolved in 30 ml of aprotic solvent (tetrahydrofuran). Nitrogen was bubbled through and 1.6 g sodium hydride was added, with continuous agitation. At the end of the oxidation reaction the mixture was hydrolyzed, followed by extraction by the method described in Example 1.

The resulting product was crystallised from diethyl ether, yielding 5.6 g of dihydroquinidinone crystals having a melting point of 86°–90° C.

EXAMPLE 7

6.2 g cinchonine and 5.8 g fluorenone were dissolved in 30 ml of an aprotic solvent (dimethyl formamide) in a 100-ml three-necked flask. A stream of nitrogen was bubbled through the solution for about 15 minutes, with agitation with a magnetic agitator.

Next, 2.5 g sodium amide was progressively added, with continuous agitation. The development of the oxidation reaction was followed by thin-layer chromatography. When the reaction was practically complete, the mixture was hydrolysed with 60 ml distilled water, followed by extraction with benzene. After washing with water, the organic phases were extracted with dilute hydrochloric acid.

The aqueous phases were made alkaline and then extracted with chloroform. After drying on sodium sulphate and filtering, the chloroform was evaporated.

62. g crude cinchonidinone (an oily liquid) was thus obtained. The yield of crude product was quantitative. The yield of pure cinchonidinone, crystallised from diethyl ether and then from ethanol, was 81%.

Cinchonidinone melts at 133°–4° C.

RMN spectrum (CDCl₃ 60 MHz) ppm = 1.1–3.2 (1 OH) 4.16 (1H, t), 5.0 (2H), 5.93 (1H), 7.6 to 9.0 (aromatic H).

What we claim is:

1. A method of oxidizing cinchona alkaloids comprising the step of reacting a ketone represented by the formula: $R_3COR_4$ in which $R_3$ and $R_4$ are the same or different and denote a branched alkyl group, an aryl group or $R_3$ and $R_4$ together with the carbonyl group form a condensed ring or a carbon or heterocyclic ring having 5 to 7 atoms with a cinchona alkaloid in the presence of a strong base in an aprotic solvent.

2. A method according to claim 1 wherein an excess of ketone is used.

3. A method according to claim 1 wherein the ketone is benzophenone, fluorenone or t-butyl ketone.

4. A method according to claim 3 wherein an excess of said ketone is used.

5. A method according to claim 1 wherein the strong base is an alkali-metal hydride or amide in excess.

6. A method according to claim 1 wherein the aprotic solvent is chosen from among hexamethyl phosphotriamide, dimethyl sulphoxide, dimethyl formamide, a hydrocarbon, an open-chain or cyclic ether, or a mixture of these solvents.

7. A method according to claim 1 wherein the reaction is carried out at ambient temperature.

8. A method according to claim 1 wherein quinine is treated with fluorenone or benzophenone in the presence of an alkali-metal hydride in an aprotic solvent.

9. A method according to claim 1 wherein the reaction is carried out in an inert atmosphere.

10. A method according to claim 1 wherein said cinchona alkaloid has the formula:

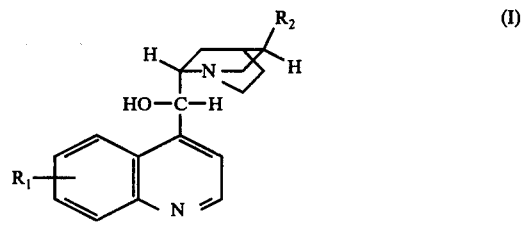

in which $R_1$ denotes hydrogen, a lower alkyl group, a hydroxy group or an alkoxy group, and $R_2$ denotes a lower alkyl group or a lower alkenyl group.

11. A method of chemically converting cinchona alkaloids to their corresponding stereo isomers comprising the steps of
   (a) oxiding the cinchona alkaloids by reaction with a ketone in the presence of a strong base in an aprotic solvent, and
   (b) reducing the oxidized cinchona alkaloids to their corresponding stereoisomers.

12. A method according to claim 11 wherein the oxidation and reduction are performed in a single stage without isolating the intermediate 9-oxo compounds.

13. A method of oxidizing cinchona alkaloids comprising the step of reacting said cinchona alkaloids with a ketone of the formula

wherein $R_3$ and $R_4$ are the same as different and denote a branched alkyl group, an aryl group, or $R_3$ and $R_4$ together with the carbonyl group form a condensed ring or a carbon or heterocyclic ring having 5 to 7 atoms, said reacting being carried out in the presence of a strong base selected from the group consisting of alkali-metal hydrides and amides, in an aprotic solvent.

* * * * *